United States Patent [19]

Schwartz

[11] Patent Number: 5,580,555
[45] Date of Patent: Dec. 3, 1996

[54] REGENERATION OF INJURED CENTRAL NERVOUS SYSTEM AXONS

[75] Inventor: Michal Schwartz, Rehovot, Israel

[73] Assignee: Yeda Research and Development Co. Ltd., Rehovot, Israel

[21] Appl. No.: 424,604

[22] Filed: Jan. 17, 1995

Related U.S. Application Data

[63] Continuation of Ser. No. 65,445, May 24, 1993, abandoned, which is a continuation of Ser. No. 511,281, Apr. 23, 1990, abandoned.

[51] Int. Cl.$^6$ .................... A61N 7/00; A61K 45/05; A61K 38/21
[52] U.S. Cl. ............ 424/85.1; 424/85.2; 424/85.5; 607/89
[58] Field of Search ................ 424/85.1, 85.2, 424/85.5; 604/20; 607/89

[56] References Cited

U.S. PATENT DOCUMENTS

| | | | |
|---|---|---|---|
| 4,525,340 | 6/1985 | Lange et al. | 424/16 |
| 4,808,402 | 2/1989 | Leibovich et al. | 424/423 |
| 4,879,111 | 11/1989 | Chong | 424/85.2 |
| 4,966,144 | 10/1990 | Rochkind et al. | 128/395 |

OTHER PUBLICATIONS

Assia, E. et al "Temporal parameters of low energy laser irradiation for optimal delay of post–traumatic degeneration of rat optic nerve", *Brain Research*, 476 (1989), 205–212.
Hadani, et al. PNAS, USA 81:7965–7969, 1984.
Schwartz, et al., Science 228:600–603, 1985.
Robbins, et al. J. Immunol. 139(8):2593–2597, 1987.
Selmaj et al., Annals Neurology 23(4):339–346, 1988.
Assia, et al, 1989, "Temporal parameters of low energy . . . " Brain Research 476:205–212.

*Primary Examiner*—Lynette F. Smith
*Attorney, Agent, or Firm*—Browdy and Neimark

[57] ABSTRACT

Administration of tumor necrosis factor to the site of injured central nervous system axons will result in facilitation of the regeneration of axons across the site of the injury. Recombinant human tumor necrosis factor is the preferred substance for such use.

8 Claims, 2 Drawing Sheets

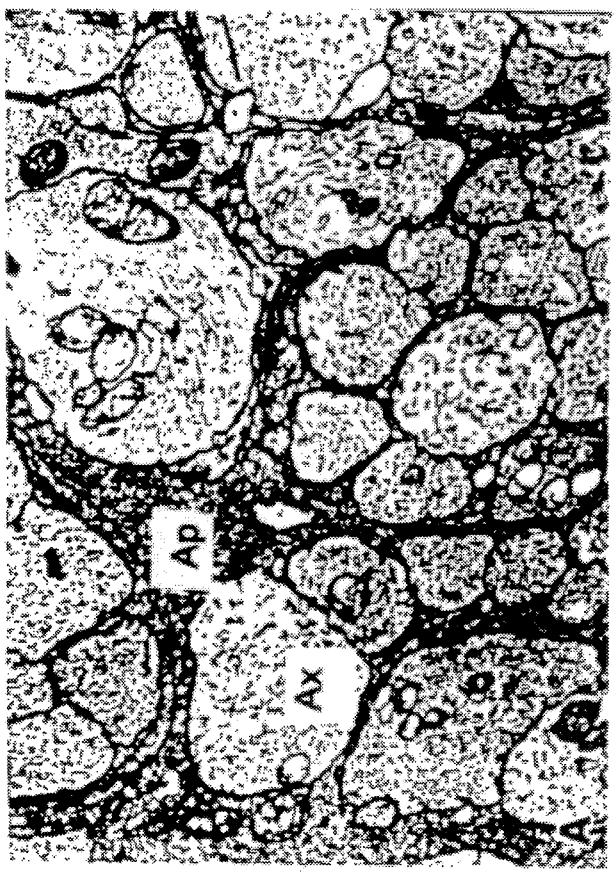
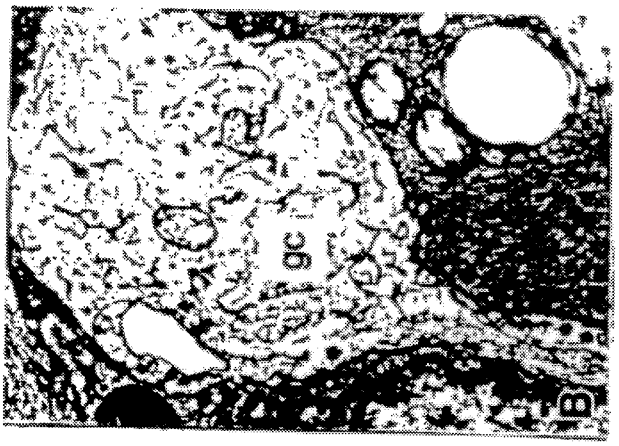

REGENERATION OF INJURED CENTRAL NERVOUS SYSTEM AXONS

CROSS-REFERENCE TO RELATED APPLICATIONS

This application is a continuation of application Ser. No. 08/065,445, filed May 24, 1993, now abandoned, which is a continuation of application Ser. No. 07/511,281, filed Apr. 23, 1990, now abandoned.

FIELD OF THE INVENTION

The present invention relates to the regeneration of mammalian central nervous system (CNS) axons.

BACKGROUND OF THE INVENTION

Mammalian CNS neurons have a negligible capacity to regenerate after lesions. In contrast, neurons in the CNS of lower vertebrates and in the peripheral nervous system (PNS) of mammals are endowed with a high post-traumatic capacity to regenerate. In the goldfish visual system, the retinal ganglion cells regenerate severed axons and make functional connections with their appropriate targets. The regenerated axons become myelinated and form their normal pattern of synaptic contacts with their targets. In mammals, however, optic nerve injury leads to the death of most of the axotomized neurons and the failure of the surviving cells to regrow their axons.

The differences in regenerative capacity have been attributed to the different compositions of the respective cellular environments and to different responses to injury the non-neuronal cells display, which range from supportive and permissive to nonsupportive and hostile for regeneration. The same cell type may support or inhibit regeneration, depending on its state of maturity or differentiation. Astrocytes and oligodendrocytes are examples of cells in which such a dichotomy is manifested. In developing and in spontaneously regenerating nerves, these cells support (astrocytes) and permit (oligodendrocytes) growth. However, in nonregenerating adult mammalian nerves, astrocytes form the nonsupportive scar tissue; and the mature oligodendrocytes inhibit axonal growth. Maturation of these cells may be regulated differently during development than after injury.

Schnell et al, *Nature*, 343: 269–72 (1990), report that CNS white matter, cultured oligodendrocytes (the myelin producing cells of the CNS), and CNS myelin itself are strong inhibitors of neuron growth in culture, a property associated with defined membrane-bound surface proteins on myelin and oligodendrocytes. Monoclonal antibodies which neutralize the inhibitory effect of these proteins were implanted intracerebrally into rats. After transection of the cortico-spinal tract, massive sprouting occurred at the lesion site and fine axons and fascicles were observed up to 7–11 mm from the lesion.

Axotomized mammalian central neurons have been shown to regenerate their axons over long distances, if special conditions are provided by replacement of the optic nerve by a segment of a peripheral autologous nerve.

Prior work of the present inventor and others has shown that the CNS of lower vertebrates, specifically regenerating fish optic nerve, is a source of factors which, when applied at the appropriate time and in appropriate amounts to injured mammalian adult optic nerves, can support regenerative axonal growth. See Schwartz et al, *Science*, 228: 600–603 (1985); Hadani et al, *Proc. Natl. Acad. Sci. U.S.A.*, 81: 7965–69 (1984); Lavie et al, *Brain Res.*, 419: 166–173 (1987); Solomon et al, *Metab. Pediatr. Syst. Ophthalmol.*, 11: 1–2, 31–2 (1988); and Cohen et al, *Neurosci. Res.*, 22: 269–273 (1989).

Robbins et al, *J. Immunol.*, 139, (8): 2593–7 (1987), have reported that stimulation of rat astrocytes in vitro resulted in the generation of a cytotoxic factor that is functionally similar to tumor necrosis factor. They also report that human recombinant tumor necrosis factor has cytotoxic activity directed against rat oligodendrocytes. Selmaj et al, *Ann. Neurol.*, 23, (4): 339–46 (988) reported on the testing of recombinant human tumor necrosis factor (rhTNF) for its effect on myelinated cultures of mouse spinal cord tissue. They found that rhTNF induced delayed-onset oligodendrocyte necrosis and a type of myelin dilatation.

Despite substantial research efforts worldwide, no safe and effective means for causing CNS regeneration in mammals, and particularly humans, has yet been developed. Such a means, and particularly a pharmaceutical which can be injected at the site of desired regeneration would be greatly desirable in order to alleviate post-traumatic paraplegia or quadraplegia, blindness, deafness, surgically associated axotomy, etc.

SUMMARY OF THE INVENTION

Accordingly, it is an object of the present invention to eliminate the aforementioned deficiencies of the prior art.

It is another object of the present invention to provide a method for regenerating injured central nervous system axons in mammals.

It is a further object of the present invention to provide a method for the treatment of post-traumatic injury of CNS nerves.

It is yet another object of the present invention to provide a composition for use in the regeneration of injured central nervous system axons.

These and other objects will become evident upon consideration of the following description of the drawings and the preferred embodiments.

It has now been found that tumor necrosis factor (TNF) will facilitate axonal regeneration across a site of injury and distally to it. Accordingly, the present invention provides use of TNF in the preparation of a medicament for use in the regeneration of CNS axons in mammals. A suitable use for the medicament is the regeneration of injured human CNS axons.

BRIEF DESCRIPTION OF THE DRAWINGS

FIGS. 1A–1D are electron micrographs from a cross-section of experimental TNF-treated nerves, from an area within the second millimeter distal to the site of injury, showing the characteristics of newly growing axons. FIG. 1A shows abundant unmyelinated axons embedded in a typical astrocytic environment; FIG. 1B shows structures resembling growth cones embedded in astrocytic processes; FIG. 1C shows unmyelinated axons in an early process of remyelination by dark cytoplasm of oligodendrocytes; and FIG. 1D shows control injured but not treated nerves, the area being completely degenerative, containing astrocytic processes and degenerating axons. The identified portions are axons (Ax), astrocytic process (Ap), growth cone (gc) and glial scar (gs).

DETAILED DESCRIPTION OF PREFERRED EMBODIMENTS

Figure 2:
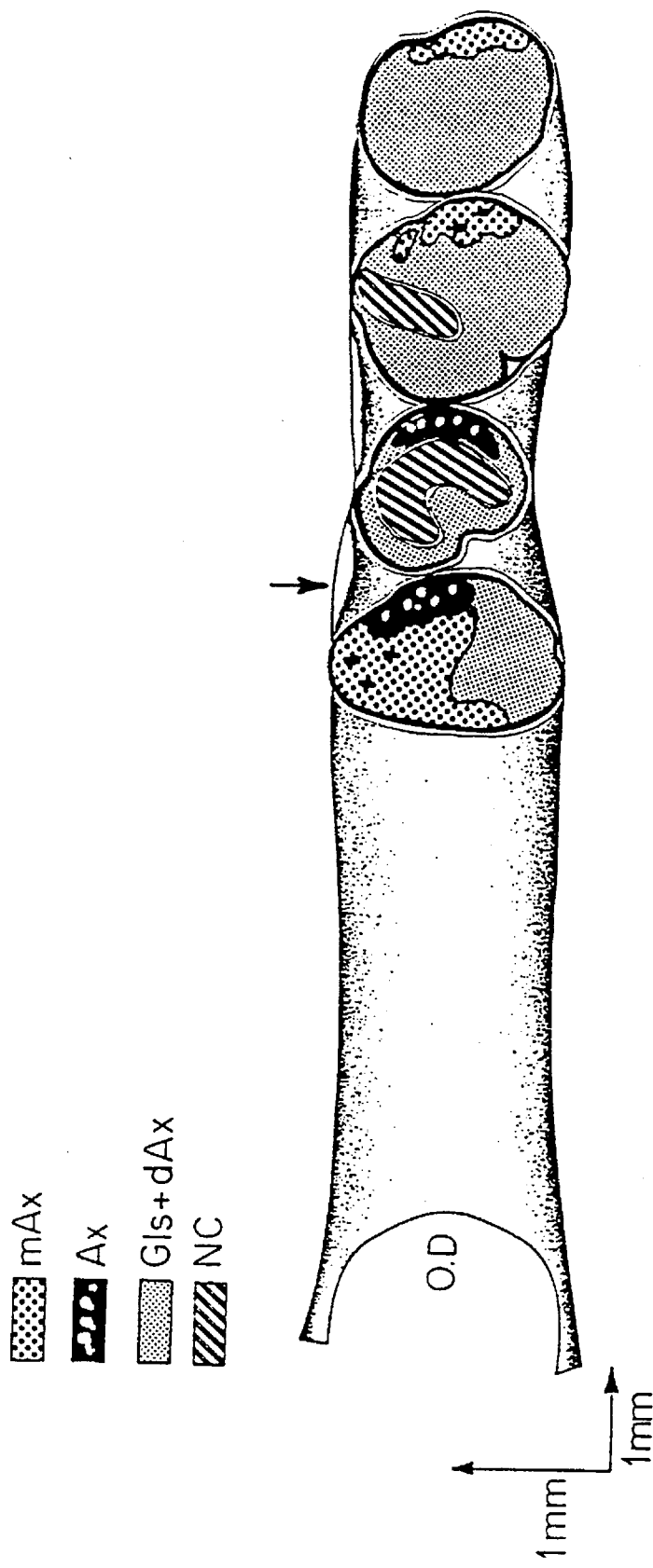
FIG. 2 is a three-dimensional reconstruction of TNF-treated nerves, 6 weeks postoperatively. Thin sections of adult rabbit optic nerve were cut, mounted on grids, photographed at x 140 and montages were constructed at each level. The compartments that could be identified in each cross-section contained newly growing axons (Ax) and myelinated axons (mAx); nitrocellulose (NC); and glial scar and degenerating axons (GLS+dAx).

Regeneration of axons at the site of a CNS injury is permitted by the administration to the area of the injury of a tumor necrosis factor (TNF). While it is preferred that the TNF be of the same species as the mammal being treated, this is not critical. Indeed, human TNF was used in the rabbit experiments detailed below. Modified TNF, i.e., a TNF protein having amino acids added, deleted or substituted as compared to native human TNF, as well as closely related cytokines which may be known by other names, or such TNF proteins which have added moieties or other peptide sequences to improve their physical properties for use in a pharmaceutical composition, may be used as a substitute for the TNF used in the present invention as long as such modified proteins maintain the function of TNF which is used in accordance with the present invention to facilitate regeneration of CNS axons. The applicability of any such TNF-variant may be readily tested, without undue experimentation, by means of an in vitro test for selective oligodendrocyte cytotoxicity. While it is not definitely known that it is the oligodendrocyte cytotoxicity of TNF which causes the regenerative effects of the present invention, it is believed that the existence of such function in vitro will be a valid predictor of its effectiveness in facilitating regeneration in vivo.

Thus, when the term "a tumor necrosis factor" is used throughout the present specification and claims, it is understood to include native tumor necrosis factor of any species, recombinant tumor necrosis factor of any species, modified TNF, and related cytokines, which have the property of facilitating the regeneration of injured mammalian axons in vivo, which function may be predicted by means of the in vitro test for selective cytotoxicity to oligodendrocytes.

The TNF may be obtained by any convenient technique. For example, it may be obtained by the process of Mathews et al, *Br.J.Cancer*, 42: 416–422 (1980) or Green et al, *J.Natl.Cancer Inst.*, 59 (5): 1519–1522 (1977). The TNF is preferably obtained by recombinant DNA technologies. Recombinant human tumor necrosis factor (rhTNF) is presently commercially available.

The TNF is used in a quantity and purity sufficient to facilitate regeneration of CNS axons in mammals, particularly humans. The TNF is administered in any manner which is calculated to bring the factor to the vicinity of the injured axons to be regenerated. Preferably, the TNF is injected in a pharmaceutically acceptable liquid carrier directly to the site. Alternatively, an implant bearing the TNF may be surgically inserted. Such an implant may consist of any material, such as nitrocellulose, which will absorb TNF like a sponge and slowly release it at site of implantation. Other means of delivery will be apparent to those skilled in this art and are intended to be comprehended within the scope of the present invention.

The amount of the TNF to be administered to any given patient depends on a variety of factors, such as the injury being treated, the site of injured axons it is wished to regenerate and the condition of the patient. Typically, however, the TNF is administered at a dose of about 100 units, as a single injection or soaked onto nitrocellulose or any other adsorbable carrier. Precise dosages will be empirically determined.

The TNF is preferably administered as soon as possible after the injury being treated. Thus, it is preferably used for acute injury rather than chronic injury. It will be more difficult to facilitate regeneration in accordance with the present invention the longer a period of degeneration has existed.

While the administration of TNF alone shows good results, such treatment may be combined with any type of concomitant therapy which may tend to augment its effects. For example, irradiation of the injury site with low energy laser, preferably He-Ne laser (5 min/day, 35mW) can delay the post-traumatic process of the degeneration and thereby delay scar formation. See Assia et al, *Brain Res.*, 476: 205–212 (1988).

The various injuries which can be treated in accordance with the present invention are myriad and will be readily apparent to those of ordinary skill in the art. Without limitation, there may be mentioned spinal cord injuries, injuries to the optical nerve or to the aural nerves, etc. Injury to CNS neurons during neurosurgery or caused by tumors may also be treated by means of the present invention.

For the purpose of the present invention, the TNF may be formulated with any pharmaceutically or veterinarily acceptable carrier or diluent. The TNF may be presented as an aqueous solution, for example as a sterile aqueous solution. A solution or powder containing TNF may be stabilized by means of a stabilizing agent. Various formulations for TNF are already known for other indications. Such formulations may also be used for the purpose of the present invention as long as the desired function of the TNF is not affected thereby.

The following Example illustrate the invention.

EXAMPLE 1

Adult rabbits (albino, Weizmann Institute Animal House) were deeply anesthetized with xylazine (5 mg/kg) and ketamine (35 mg/kg). The left optic nerves were exposed as previously described (Solomon et al, *J. Neurosci. Meth.*, 12: 259–262 (1985)) and transected except for the meningeal membrane at a distance of 5–6 mm from the eyeball using a sharpened needle. In all operated nerves, a piece of nitrocellulose, 3 mm long and 1 mm wide, was inserted at the site of the injury. For the experimental group of rabbits, the nitrocellulose was soaked with rhTNF (100 U/nerve; $6 \times 10^7$ U/mg) for 1 hour prior to the insertion. For the control group the nitrocellulose was soaked in the medium used to dilute the TNF (DMEM), free of any active substances. Beginning within 30 min of surgery, the experimental animals were also daily treated for ten days with low energy He-Ne laser irradiation (632.8 mm, 35 mw) for 5 min per day.

The experimental and control injured nerves were examined qualitatively and quantitatively at 6 weeks postoperatively by transmission electron microscopy. Such an analysis allows distinction between newly growing axons and spared axons. Quantitative analyses were carried out as previously described (Lavie, V. et al, *J. Comp. Neurology*, 298: 293–314 (1990). Briefly, systematically selected thin sections were photographed by the electron microscope at low magnification (x 140), which permitted identification of the newly growing axons (including unmyelinated and thinly myelinated axons).

FIG. 1 includes photographs taken from a cross-section of experimental TNF-treated nerves, from an area within the second millimeter from the site of injury. These pictures depict characteristics of newly growing axons, including abundant unmyelinated axons embedded in a typical astrocytic environment (FIG. 1A), structures resembling growth cones embedded in astrocytic processes (FIG. 1B), and axons in early stages of myelination by oligodendrocyte dark cytoplasm (FIG. 1C). The unmyelinated axons were counted in four regions along the nerve: 1 mm before the site of injury, at the end of the nitrocellulose, 2 mm distally to it, and at the area deep into the distal stump. Table 1 shows the obtained results.

TABLE 1

Number of unmyelinated and myelinated axons in a TNF-treated nerve

| Distance from the globe | Number of counted axons*** | | |
|---|---|---|---|
| (mm) | Unmyelinated | Myelinated | Total |
| 6 | 7530 | 31357 | 38887 |
| 8 | 8466 | 591 | 9057 |
| 10* | 200 | 2272 | 2472 |
| 12 | — | 2732 | 2732 |

The results represent the analysis of one nerve by the sampling method. These results were qualitatively reproducible in 3 additional nerves.
*The last region in which nitrocellulose could be observed.
**The site of injury located between the 6 and 7 mm distally to the globe.
***In control animals, no unmyelinated axons could be observed in the section taken at the same distance as in the experiment.

The maximal number of unmyelinated axons is seen within the second millimeter distal to the site of injury (8466). In control untreated animals, at the same distance from the lesion, no unmyelinated or myelinated axons could be observed. The number of unmyelinated axons decreases with the increase in the distance from the site of the injury. The apparent increase in number of myelinated axons in the area 4 mm distally to the lesion relative to the 2 mm distance, might be due to myelination of part of the growing axons, or axons which were injured but their degeneration had not reached the examined area (4 mm on from the injury). Three-dimensional reconstruction of the nerve (FIG. 2) showed that the area occupied by the viable unmyelinated and myelinated axons, as well as their total number decreases upon increasing distance from the site of injury, thus emphasizing that the observed unmyelinated axons are, indeed, newly growing axons, rather than spared axons that have lost their myelin sheaths.

EXAMPLE 2

S.P.D. rats, 3 months old weighing 300 g, were anesthetized with a loading dose of 15 mg Ketamine and 4 mg Rompun 2%. After performing a laminectomy at $T_{12}$ level, the left hemicord was crushed with Weck MICRO-CLIP 6 mm×1 mm (catalog no. 065145) for 30 seconds. No gross anatomical disruption was noticed after the crush.

Following the crush, 10 μl (100 U) of TNF were injected at the site of injury, into the cord, after which the wound was closed.

Eight weeks later the rats were anesthetized again and after a partial laminectomy at $T_6$ level, 10 μl horseradish peroxidase (HRP) 30% were injected into the cord, and the site of injection was sealed by silicone cream.

Twenty four hours after the HRP injection, the rats were sacrificed and perfused with paraformaldehyde. The cord was removed and longitudinal sections, 75 microns, were cut with a VIBRATOME. The sections were developed by cobalt intensification as described by Meshulam in "Tracing Neural Connections with Horseradish Peroxidase", IBRO Handbook Series, *Methods in Neuroscience,* John Wiley and Sons, 1982.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for facilitating the regeneration of injured central nervous system axons in a mammal comprising administering to the site of the injury an effective quantity of a tumor necrosis factor within a time after injury that the administration of the tumor necrosis factor is still effective and irradiating the injury site with low energy laser concomitantly with said step of administering tumor necrosis factor.

2. A method in accordance with claim 1, wherein the mammal is a human.

3. A method in accordance with claim 1, wherein the tumor necrosis factor is recombinant human tumor necrosis factor.

4. A method in accordance with claim 1, wherein the tumor necrosis factor is administered by direct injection to the site of the injury.

5. A method in accordance with claim 1, wherein the injured central nervous system axons are spinal cord axons.

6. A method in accordance with claim 1, wherein the injured central nervous system axons are optical nerve axons.

7. A method in accordance with claim 1, wherein said injured central nervous system axons consist of a severed nerve.

8. A method in accordance with claim 1, wherein the injured central nervous system axons are aural nerve axons.

* * * * *